US008187617B2

(12) United States Patent
Howard et al.

(10) Patent No.: US 8,187,617 B2
(45) Date of Patent: *May 29, 2012

(54) IMMEDIATE RELEASE COMPOSITIONS AND METHODS FOR DELIVERING DRUG FORMULATIONS USING WEAK ACID ION EXCHANGE RESINS IN ABNORMALLY HIGH PH ENVIRONMENTS

(76) Inventors: William Wayne Howard, Morristown, NJ (US); Russell Francis Somma, Sparta, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/807,434

(22) Filed: Sep. 3, 2010

(65) Prior Publication Data

US 2011/0065742 A1    Mar. 17, 2011

Related U.S. Application Data

(60) Provisional application No. 61/276,366, filed on Sep. 11, 2009.

(51) Int. Cl.
*A61K 9/00* (2006.01)
(52) U.S. Cl. ......... 424/400; 424/465; 424/452; 424/483
(58) Field of Classification Search ........................ None
See application file for complete search history.

(56) References Cited

U.S. PATENT DOCUMENTS

| 5,811,126 | A * | 9/1998 | Krishnamurthy | 424/498 |
|---|---|---|---|---|
| 5,811,436 | A | 9/1998 | Leonard et al. | 514/321 |
| 2004/0126324 | A1 * | 7/2004 | Hughes | 424/10.1 |
| 2005/0036977 | A1 * | 2/2005 | Gole et al. | 424/76.1 |
| 2008/0075784 | A1 * | 3/2008 | Friesen et al. | 424/493 |
| 2008/0118570 | A1 * | 5/2008 | Liu et al. | 424/490 |
| 2010/0092562 | A1 * | 4/2010 | Hollenbeck et al. | 424/488 |

OTHER PUBLICATIONS

Wikipedia "Organic Base" (pp. 1-2) retrived online Jan. 17, 2012.*
Wikipedia "Base" (p. 1) retrived online Jan. 17, 2012.*
Wikipedia "Glycine" (p. 1) retrived online Jan. 17, 2012.*
Wikipedia "Inorganic Chemistry" (p. 1) retrived online Jan. 17, 2012.*
"Ferric Oxide" product sheet from GFS Chemicals (pp. 1-2) retrieved online on Jan. 17, 2012.*
Agarwal et al., "Studies of ion-exchange resin complex of chloroquine phonsphate", *Drug Development and Industrial Pharmacy*, 25(7), 773-776 (2000).
Atanassoff P., et. al., "The time course of gastric pH changes induced by omeprazole and ranitidine", *Anethesia Analgesics*, 80, 975-979, 1995.
Bajpai S K et al.,"Ion exchange resins in drug delivery", . In *Ion Exchange and Solvent Extraction, A Series of Advances*, 18, CRC Press, 2007.
Elder D.P., et al., "Development of a palatable liquid formulation of a bitter tasting drug using ion exchange resins for taste masking" In *Ion Exchange at the Millennium*, Imperial College Press, London, 2000.
Jaskari T., et al., "Ion-exchange fibers and drugs: an equilibrium study" *Journal of Controlled Release*, 70, 219-229, 2001.
Kircheiner J. et al., Relative potency of proton-pump inhibitors—comparison of effects on intragrastric pH *European Journal of Clinical Pharmacology*, 69, 19-31, 2009.
Liu Z., et al., "A study of doxorubicin loading onto and release from sulfopropyl dextran in-exchange microspheres." *Journal of Controlled Release*, 77, 213-224, 2001.
Schlichting, D., "Ion exchange resin salts for oral therapy" *Journal of Pharmaceutical Sciences*, 51(2), 134-136, 1962.
Smout A., et al., "Effect of evening dose of regular and effervescent formulations of ranitidine or cimetidine on intragastric pH in health volunteers." *Aliment Journal*, 9, 51-56, 1995.
Sprockel, O. L., et al., "Evaluation of sustained release aqueous suspensions containing microencapsulated drug-resin complexes.", *Drug Development and Industrial Pharmacy*, 15(8), 1275-1287, 1989.
Sriwongjanya M., et al., "Effect of ion exchange resins on the drug release from matrix tablets.", *European Journal of Phamaceutics and Biopharmaceutics*, 46, 31-327, 1998.

* cited by examiner

*Primary Examiner* — Bethany Barham
(74) *Attorney, Agent, or Firm* — Sheldon Kavesh

(57) ABSTRACT

Immediate release compositions and methods for delivering drug formulations using weak acid ion exchange resins in abnormally high pH environments.

16 Claims, 13 Drawing Sheets

IMMEDIATE RELEASE COMPOSITIONS AND METHODS FOR DELIVERING DRUG FORMULATIONS USING WEAK ACID ION EXCHANGE RESINS IN ABNORMALLY HIGH PH ENVIRONMENTS

CROSS REFERENCE TO RELATED APPLICATIONS

This application claims the benefit of U.S. Provisional Application Ser. No. 61/276,366 filed Sep. 11, 2009. It is related to U.S. application Ser. No. 12/799,259 filed Apr. 21, 2010.

BACKGROUND OF THE INVENTION

The present invention relates to the use of weak acid ion exchange resins (IER) to create an immediate release (IR) drug delivery system using release enhancers to overcome the pH dependent release characteristics normally associated with weak acid resins.

Formulations containing weak acid ion exchange resins are frequently used for immediate release of pharmaceutical agents in a patient's stomach. However, release from weak acid resins is slowed and/or reduced at higher than normal stomach pH levels. High pH levels could occur if the patient is taking medications such as proton pump inhibitors (PPIs) or has a disease state that induces hypochlorhydria or achlorhydria. In either case, a weak acid formulation may not release the medicament at a rate or to an extent adequate to achieve the desired therapeutic effect.

Approximately 60 million prescriptions were written for PPIs in 2006. Additionally, in the U.S., another 10 million people were reported to have self medicated with PPIs in 2008. Furthermore, about one in three adults used antacids on a regular basis. Collectively, these statistics suggest that close to 100 million people in the U.S. could be taking a drug that could significantly interfere with the release profile of a weak acid IER formulation. The history of prior art dosage forms indicates that a serious need exists for a novel and useful solid oral dosage form that provides an unexpected advancement in the science of IER dosage forms. For example, prior art dosage forms lack the ability to provide the immediate release properties of weak acid IER formulations when administered to a patient with stomach pH environments at about 1.5 to 2.0 and above. Surprisingly and unexpectedly, weak acid resinates can be formulated to have immediate release characteristics at pH levels above about 1.5 to 2.0. The present invention creates a release enhancing weak acid resin drug formulation by adding a release enhancing agent to the formulation to increase the rate and extent of drug release from the formulation such that it meets an a priori definition of immediate release.

SUMMARY OF THE INVENTION

Surprisingly it has been found that by adding a release enhancing agent with a strong affinity for the ionic resin to a weak acid resin drug formulation, much more rapid and complete release of a resinated drug can be attained in abnormal gastric fluid than otherwise would occur without the presence of the release enhancing agent in abnormal human gastric fluid wherein the pH is much higher than normal due to the use of drugs such as PPI or the presence of disease states such as *H. pylori* or atrophic gastritis that can lead to hypochlorhydria and achlorhydria.

Thus, one can attain the rapid release properties of weak acid resinates while retaining the low sensitivity to pH change associated strong acid resins by adding a release enhancing agent to the weak acid drug formulation.

Immediate release is defined as at least 80% release of a pharmaceutically active agent within 45 minutes in a standard dissolution apparatus according to the USP 31 NF 26 section 711.

In a first embodiment, the invention is a solid oral dosage pharmaceutical composition comprising (i) at least one pharmaceutically active agent bound to a weak acid ion exchange resin and (ii) a release enhancing agent.

In a second embodiment, the invention is a solid oral dosage pharmaceutical composition comprising (i) at least one pharmaceutically active agent bound to a weak acid ion exchange resin to form a weak acid ion exchange resinate (ii) a release enhancing agent; wherein said composition is capable of an immediate release of said at least one pharmaceutically active agent from said weak acid ion exchange resinate when administered to a patient with a stomach pH of at least about 1.5.

In a third embodiment, the invention is a solid oral dosage pharmaceutical composition comprising (i) at least one pharmaceutically active agent bound to a weak acid ion exchange resin and (ii) a release-enhancing agent, wherein said pharmaceutical composition is useful for oral administration.

In a fourth embodiment, the invention is a solid oral dosage pharmaceutical composition comprising (i) at least one pharmaceutically active agent bound to a weak acid ion exchange resin and (ii) a release-enhancing agent, wherein said pharmaceutical composition is useful for patients having normal stomach acid pH of at least about 1.5 to 2.0.

In a fifth embodiment, the invention is a solid oral dosage pharmaceutical composition comprising (i) at least one pharmaceutically active agent bound to a weak acid ion exchange resin and (ii) a release-enhancing agent, wherein said pharmaceutical composition is useful for patients having a an ailment selected from the group consisting of *Helicobacter pylori* infection, atrophic gastritis, hypochlorhydria and achlorhydria.

In a sixth embodiment, the invention is a solid oral dosage pharmaceutical composition comprising (i) at least one pharmaceutically active agent bound to a weak acid ion exchange resin and (ii) a release-enhancing agent, wherein said pharmaceutical composition is useful for patients selected from the group consisting of patients who have been administered a member of the group consisting of a proton pump inhibitor, an H2 receptor antagonist, and an antacid, within the preceding 24 hours.

In a seventh embodiment, the invention is a method of treating a patient for a condition with a pharmaceutically active agent effective for treating said condition, said method comprising orally administering a solid oral dosage pharmaceutical composition comprising (i) at least one pharmaceutically active agent bound to a weak acid ion exchange resin and (ii) a release-enhancing agent In an eighth embodiment, the invention is a method of treating a patient with a stomach pH of at least about 1.5 comprising administration of the solid oral dosage composition of claim 1 wherein said administration results in immediate release of said pharmaceutically active agent from said weak acid ion exchange resinate.

DETAILED DESCRIPTION OF THE INVENTION

Figure 1:
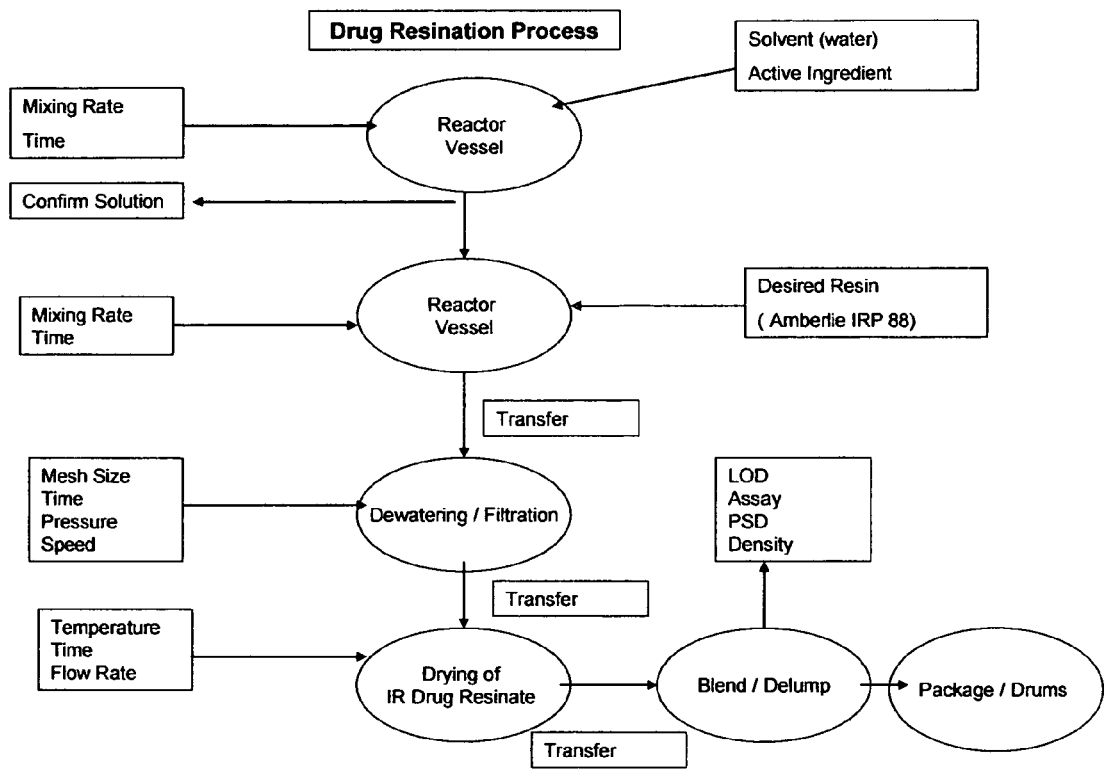
FIG. 1 is a flow chart that illustrates a process for creating a drug/resin complex, the drug resination process.

In a first embodiment, the invention is a solid oral dosage pharmaceutical composition comprising (i) at least one pharmaceutically active agent bound to a weak acid ion exchange resin and (ii) a release-enhancing agent.

The pharmaceutical compositions of the invention are characterized by faster, and/or more complete, drug release compared to a weak acid resin formulation without the release enhancing agent in pH environments at or above about 1.5 to 2.0. When administered to a patient, the release-enhancing agent results in immediate release of the pharmaceutically active agent(s) from the weak acid ion exchange resin in pH environments at or above about 1.5 to 2.0.

The pharmaceutical composition can be formulated, for example, as a capsule or compressed tablet. The inventive compositions are preferably in a solid oral dosage form, such as a tablet, caplet, capsule, orally disintegrating tablet, powder, consumable film or any other dosage form, containing at least one pharmaceutical agent bound to an ion exchange resin and at least one release-enhancing agent. The composition is preferably swallowed without forming a liquid state of the active drug substance prior to ingestion through the oral cavity and into the gastric system.

The invention includes compositions having a single pharmaceutically active agent and also fixed combination products containing more than one pharmaceutically active agent. Furthermore, the invention includes compositions including both an IR component and extended release (ER) component. In these embodiments, the IR component (as described above) can also be used as the nucleus to provide the extended release component through the use of an extended release coating.

The drug release kinetics of weak acid resins can be affected by higher pH levels in the gastric fluid such that the rate and/or extent of drug release can be greatly reduced. Adding a release enhancing agent to a weak acid formulation is useful for assuring that the resinated drug is released from an IER formulation when stomach acid is reduced or eliminated (hypochlorhydria and achlorhydria) by disease states such as *Helicobacter* (*H.*) *pylori* infection or atrophic gastritis.

By adding a release enhancing agent with a strong affinity for the ionic resin to the weak acid resin drug formulation can facilitate release of the resinated drug in abnormal human gastric fluid where the pH is much higher than normal due to the use of drugs such as proton pump inhibitors or the presence of disease states such as *H. pylori* infection or atrophic gastritis.

Weak acid ion exchange resins useful in the invention include, for example, Amberlite IRP88 (CAS Registry Number 39394-76-5), and DOWEX MAC-3, but other weak acid ion exchange agents may be used.

The release-enhancing agent can be, for example, an inorganic salt (e.g., a salt including $Fe^{3+}$, $Ca^{2+}$, $Mg^{2+}$, or $Fe^{2+}$) an organic base (e.g., thiamine, guanine, or cytosine), a cationic surfactant (e.g., cetyltrimethylammonium bromide (CTAB), denatonium benzoate, or benzalkonium chloride), or a nonionic surfactant (e.g., Tween 20 or Tween 80).

The pharmaceutical composition can optionally include a second ion exchange resin. This second ion exchange resin is bound to one or more pharmaceutical agents and can be coated with a extended release coating, resulting in extended release of the pharmaceutically active agent(s) from the second ion exchange resin when administered to a patient. The second ion exchange resin can be bound to the same or different pharmaceutically active agent as the first ion exchange resin.

In a second embodiment, the invention is a solid oral dosage pharmaceutical composition comprising (i) at least one pharmaceutically active agent bound to a weak acid ion exchange resin to form a weak acid ion exchange resinate (ii) a release enhancing agent; wherein said composition is capable of an immediate release of said at least one pharmaceutically active agent from said weak acid ion exchange resinate when administered to a patient with a stomach pH of at least about 1.5, and preferably at least about 2.

In a third embodiment, the invention is a solid oral dosage pharmaceutical composition comprising (i) at least one pharmaceutically active agent bound to a weak acid ion exchange resin and (ii) a release-enhancing agent, wherein said pharmaceutical composition is useful for oral administration.

In a fourth embodiment, the invention is a solid oral dosage pharmaceutical composition comprising (i) at least one pharmaceutically active agent bound to a weak acid ion exchange resin and (ii) a release-enhancing agent, wherein said pharmaceutical composition is useful for patients having normal stomach acid pH of at least about 1.5, and preferably at least about 2.

In a fifth embodiment, the invention is a solid oral dosage pharmaceutical composition comprising (i) at least one pharmaceutically active agent bound to a weak acid ion exchange resin and (ii) a release-enhancing agent, wherein said pharmaceutical composition is useful for patients having a an ailment selected from the group consisting of *Helicobacter pylori* infection, atrophic gastritis, hypochlorhydria and achlorhydria.

In a sixth embodiment, the invention is a solid oral dosage pharmaceutical composition comprising (i) at least one pharmaceutically active agent bound to a weak acid ion exchange resin and (ii) a release-enhancing agent, wherein said pharmaceutical composition is useful for patients selected from the group consisting of patients who have been administered a member of the group consisting of a proton pump inhibitor, an H2 receptor antagonist, and an antacid, within the preceding 24 hours.

In a seventh embodiment, the invention is a method of treating a patient for a condition with a pharmaceutically active agent effective for treating said condition, said method comprising orally administering a solid oral dosage pharmaceutical composition comprising (i) at least one pharmaceutically active agent bound to a weak acid ion exchange resin and (ii) a release-enhancing agent In an eighth embodiment, the invention is a method of treating a patient with a stomach pH of at least about 1.5, and preferably at least about 2 comprising administration of the solid oral dosage composition of claim 1 wherein said administration results in immediate release of said pharmaceutically active agent from said weak acid ion exchange resinate.

By "release-enhancing agent" is meant an agent that, when added to a weak acid drug resin formulation, increases the rate and/or extent of drug release than would otherwise occur without the release-enhancing agent in the same formulation.

By "pharmaceutically active agent" is meant agents other than food articles that are intended to diagnose, cure, mitigate, treat or prevent disease in man or other animals or that are intended to affect the structure or any function of the body of man or other animals that are physiologically acceptable. The agent could be a combination of drug therapies as well as a single agent.

By "physiologically acceptable" is meant those substances that are adequately tolerated without causing unacceptable negative side effects.

By "ion exchange resin" is meant an insoluble solid matrix that carries exchangeable ions with either a positive or negative charge. The trapping of ions takes place only with simultaneous releasing of other ions. Ions are exchanged in stoichiometrically equivalent amounts of other ions with the same electrical charge when the ion exchange material is in contact with an electrolyte solution.

By "resinate" is meant the complex formed when a drug exchanges an ion with a resin particle in the stoichiometric process described above and a drug/resin compound is formed.

By "weak acid ion exchange resin" is meant in a weak acid resin the ionizable group introduced to the polymer is a carboxylic acid (COOH) as opposed to the sulfonic acid group ($SO_3H$) used in strong acid resins. These resins behave similarly to weak organic acids so are weakly dissociated i.e. have fewer ions available for exchange.

By "immediate release" is meant that the pharmacologically active agent is released from the formulation immediately such that 80%, 85%, 90%, or even 95% of the pharmaceutically active agent in the formulation is released within 45 minutes when dissolution is measured according to the USP 31 NF 26 section 711.

By "extended release" is meant that the pharmaceutically active agent is released from the formulation at a controlled rate such that the formulation allows for a reduction in dosing frequency as compared to that presented by a conventional dosage form, e.g. an immediate release dosage form.

Release-Enhancing Agents

The drug-containing weak acid ion exchange resins of the invention are formulated with release-enhancing agents. These release-enhancing agents result in immediate release of the drug from the weak acid ion exchange resins in pH environments at or above 2.0. Examples of suitable release-enhancing agents are:

Inorganic Agents:
$Fe^{3+}$ (e.g. $FeCl_3$)
$Ca^{2+}$ (e.g. $CaCl_2$)
$Mg^{2+}$ (e.g. $MgCl_2$).
$Fe^{2+}$ (e.g. $FeCl_2$)
Organic agents:
Thymine
Guanine
Cytosine Pharmaceutically Active Agents The invention features methods and compositions for immediate release of pharmaceutically active agents using a weak acid ion exchange resin. Examples of such pharmaceutically active agents suitable for the compounds and methods of the inventions are:

A: Anti-tussives, e.g., benzonatate, caramiphen edisylate, chlophedianol, codeine, dextromethorphan hydrobromide, hydrocodone, levopropoxyphene, morphine codeine, ethylmorphine, dihydrocodeine, benzylmorphine, laudanum, dihydroisocodeine, nicocodeine, nicodicodeine, hydrocodone, hydromorphone, acetyldihydrocodeine, thebacon, diamorphine (heroin), acetylmorphone, noscapine, and pholcodine.

B: Narcotic analgesics, e.g., codeine, oxycodone, hydrocodone, diamorphine, pethidine, morphine, oxymorphone, nalorphine, naloxone, naltrexone, opium, hydromorphone, nicomorphine, dihydrocodeine, and papaveretum.

C: Decongestants, e.g., pseudoephedrine hydrochloride, phenylephrine bitartrate, phenylephrine hydrochloride and pseudoephedrine sulfate.

D: Non-steroidal anti-inflammatory drugs, e.g., aspirin, magnesium salicylate, diclofenac, etodolac, indometacin, nabumetone, sulindac, tolmetin, ibuprofen, ketoprofen, mefenamic acid, meclofenamic acid, phenylbutazone, piroxicam, meloxicam, celecoxib, parecoxib, rofecoxib, valdecoxib, and naproxen sodium.

E: Anti-emetic drugs, e.g., dolasetron, granisetron, ondansetron, tropisetron, palonosetron, mirtazapine, metoclopramide, cyclizine, diphenhydramine, dimenhydrinate, meclizine, promethazine, and hydroxyzine.

F: Anti-histamines, e.g., diphenhydramine, loratadine, desloratadine, meclizine, fexofenadine, pheniramine, cetirizine, promethazine, brompheniramine, clemastine fumarate and chlorpheniramine.

G: Proton pump inhibitors (PPI), e.g., omeprazole, esomeprazole, pantoprazole, lansoprazole, and rabeprazole.

H: H2 Antagonists, e.g., cimetidine, ranitidine, and famotidine.

I: Anti-depressants, e.g., citalopram, escitalopram, fluoxetine, fluvoxamine, paroxetine, sertraline, desvenlafaxine, duloxetine, milnacipran, venlafaxine, atomoxetine, mazindol, reboxetine, viloxazine, amitriptyline, clomipramine, doxepin, imipramine, trimipramine, desipramine, nortriptyline, protriptyline, moclobemide, phenelzine, and selegiline.

J: Tranquilizers, e.g., amobarbital, pentobarbital, secobarbital, phenobarbital, clonazepam, diazepam, estazolam, flunitrazepam, lorazepam, midazolam, nitrazepam, oxazepam, triazolam, temazepam, chlordiazepoxide, and alprazolam.

K: Anti-convulsants, e.g., felbamate, carbamazepine, oxcarbazepine, vigabatrin, progabide, tiagabine, topiramate, gabapentin, pregabalin, ethotoin, and phenyloin.

L: Hypnotics, e.g., zolpidem, zaleplon, zopiclone, and eszopiclone.

M: Muscle relaxants, e.g., methocarbamol, carisoprodol, chlorzoxazone, cyclobenzaprine, gabapentin, metaxalone, and orphenadrine.

N: Anti-psychotics, e.g., haloperidol, droperidol, chlorpromazine, fluphenazine, perphenazine, prochlorperazine, thioridazine, trifluoperazine, mesoridazine, promazine, triflupromazine, levomepromazine, methotrimeprazine, pimozide, chlorprothixene, flupenthixol, thiothixene, zuclopenthixol, clozapine, olanzapine, risperidone, quetiapine, ziprasidone, amisulpride, asenapine, and paliperidone.

O: Anti-microbials, e.g., EDTA, zinc compounds, triclosan, domiphen, cetyl pyridium chloride, domiphen bromide, fluorides, alexidine, and octenidine.

P: Anti-diarrheals, e.g., bismuth subsalicylate and loperamide.

R: CNS stimulants, e.g., caffeine, cocaine, and amphetamines.

S: Attention Deficit and Hyperactivity Disorder drugs, e.g., methylphenidate, dextroamphetamine sulfate, amphetamine, and atomoxetine hydrochloride.

The invention also includes methods and compositions for delivering combinations of pharmaceutically active compounds. Examples of such combinations are:

A: an anti-tussive and an antihistamine
B: an anti-tussive and a decongestant
C: an anti-tussive and an analgesic
D: an anti-tussive and an NSAID
E: an anti-tussive and an antihistamine and a decongestant
F: an anti-tussive and an antihistamine and an analgesic
G: an anti-tussive and an antihistamine and an NSAID
H: an anti-tussive and an antihistamine and a decongestant and an analgesic
I: a muscle relaxant and an analgesic
J: a muscle relaxant and an NSAID
K: a muscle relaxant and an analgesic and an NSAID
L: a PPI and an NSAID
M: an H2 antagonist and an NSAID
N: a PPI and an analgesic
O: an H2 antagonist and an analgesic Ion Exchange Resins The compositions of the invention include weak acid ion exchange resins.

Examples of suitable ion exchange resins are, for example,

A: Amberlite IRP88 (CAS Registry Number 39394-76-5) manufactured by DOW Chemical B: DOWEX Mac-3 manufactured by DOW Chemical Dosage Forms Suitable dosage forms include tablets, capsules, orally disintegrating tablets, thin films, powders, beadlets, and the like

EXAMPLES

Each of the compositions of the examples below are useful for oral administration for conditions such as normal stomach pH of about 1.5 to 2.0 or higher, *Helicobacter pylori* infection, atrophic gastritis, hypochlorhydria and achlorhydria. The compositions of the examples are also useful for patients who have been administered a proton pump inhibitor, or a H2 receptor antagonist or an antacid within the preceding 24 hours.

Example 1

Mono-Substance Hydrocodone IR Coated Intermediate

| | |
|---|---|
| Hydrocodone Resinate Intermediate* | 25 mg |
| HPMC 6 cps | 3 mg |
| Talc | 2 mg |
| Triethyl Citrate | 2 mg |
| Total Dosage Form Weight | 32 mg |

*Equivalent to Hydrocodone Bitartrate 10 mg.

The process for creating the drug/resin complex and dosage form was as follows.

500 mg of IRP-88 from Rohm and Haas (currently DOW) were added to deionized water (2.5 L) which had been heated to 85° C. The resin and water were mixed using a magnetic stirring bar until a uniform suspension was obtained. 150 mg of Hydrocodone Bitartrate was made into a solution in deionized water and then added to the resin slurry and mixed in the primary Vessel with continued mixing for 4.0 hours at 85° C. to create the hydrocodone resinate. The slurry was vacuum filtered to separate the resinate from the water. The resin particles were washed three times by re-suspending the particles in 5 liters of deionized water maintained at 85° C. The resulting washed particles were filtered and allowed to cool for 12 hours. This process was repeated in order to generate adequate amounts of the hydrocodone resinate to prepare the number of capsules required for dissolution testing. Care was taken during the cooling process to avoid cake formation by periodically mixing the resinate bed with a glass stirring rod. The resinate was then dried using a lab scale fluid bed dryer set at 55° C. inlet temperature. Drying was continued until a residual moisture content of 2.0% was obtained. Drug loading was tested and showed approximately 40% drug load or approximately 40 mg of hydrocodone per 100 mg of resinate.

The dried resinate was then formulated into hard gelatin capsules using the materials in the table above. The dried resinate was coated in a lab scale column coater using hydroxypropylmethylcellulose (HPMC) and triethyl citrate as a plasticizer. This is meant to enhance processing and protect the finished resin during subsequent capsule filling. The HPMC coating is a type which has no effect on the dissolution rate and is added as a processing aid to enhance material flow during additional manufacturing steps. The coated resin along with the remaining ingredients were blended in a lab scale diffusional mixer and filled into empty capsule shells.

FIG. 1 is an illustration of the process for creating the resinate.

Example 2

Formulation for a Commercial Hydrocodone Product

Mono-Substance IR Dosage Form, Hard Gelatin Capsule

| | |
|---|---|
| Hydrocodone Resinate Coated IR Intermediate* | 32 mg |
| Release enhancing agent | 15 mg |
| Magnesium Stearate | 2 mg |
| Colloidal Silicon Dioxide | 3 mg |
| Empty Capsule Shell #3 | 48 mg |
| Total Dosage Form Weight | 100 mg |

*Equivalent to Hydrocodone Bitartrate 10 mg.

Figure 6:
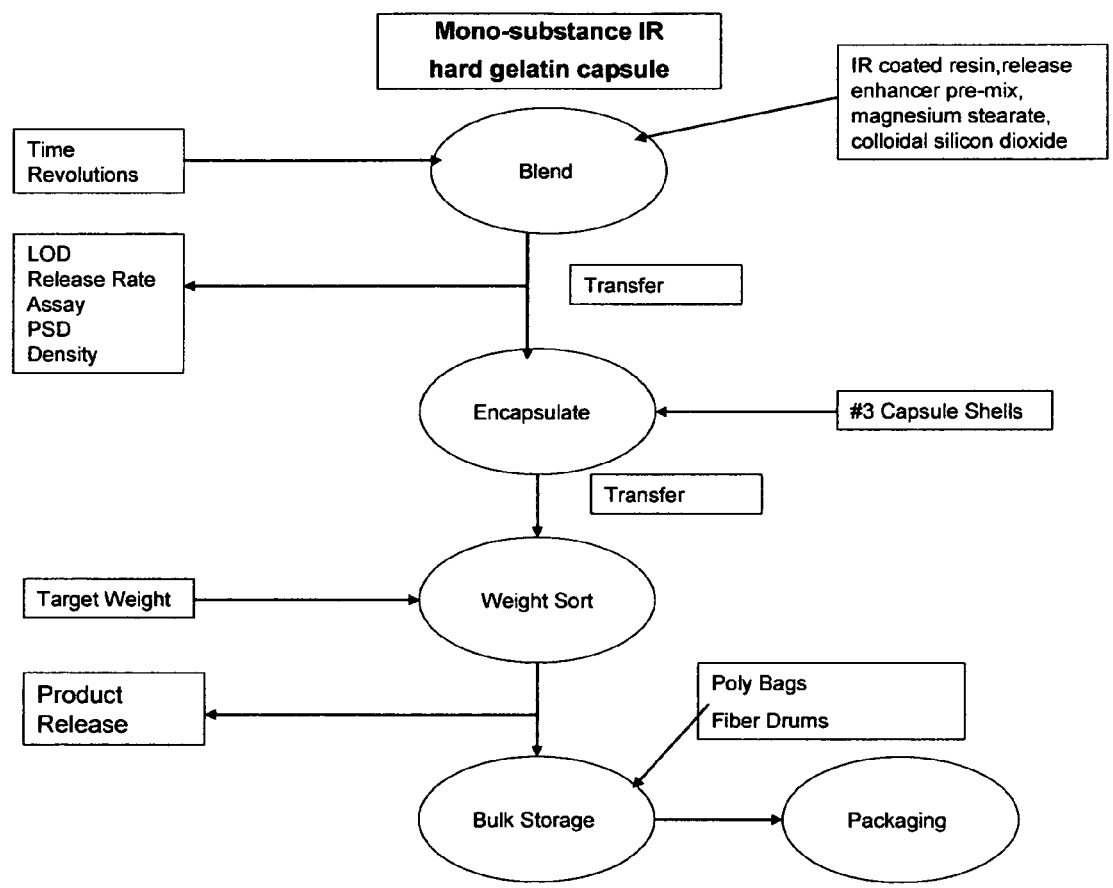
FIG. 6 is a flow chart that illustrates a process for creating an immediate release capsule dosage form containing a drug resinate and a release enhancing agent.

A mono-substance hydrocodone IR dosage form could be prepared as follows. The process begins with the coated hydrocodone resinate as specified in Example 1 and created with the processes described in FIG. 1 and FIG. 2. In the last process step, as shown in FIG. 6, the coated resinate, the release enhancing agent and the other excipients are blended and filled into hard gelatin capsules.

Example 3

Formulation for a Commercial

Mono-Substance IR Hydrocodone Dosage Form, Compressed Tablet

| | |
|---|---|
| Hydrocodone Resinate Coated IR Intermediate* | 32 mg |
| Microcrystalline cellulose | 150 mg |
| Polyplasdone XL | 10 mg |
| Release enhancing agent | 15 mg |
| HPMC 6 cps | 20 mg |
| Anhydrous lactose | 100 mg |
| Magnesium stearate | 4 mg |
| Total Dosage Form Weight | 331 mg |

*Equivalent to Hydrocodone Bitartrate 10 mg

Figure 5:
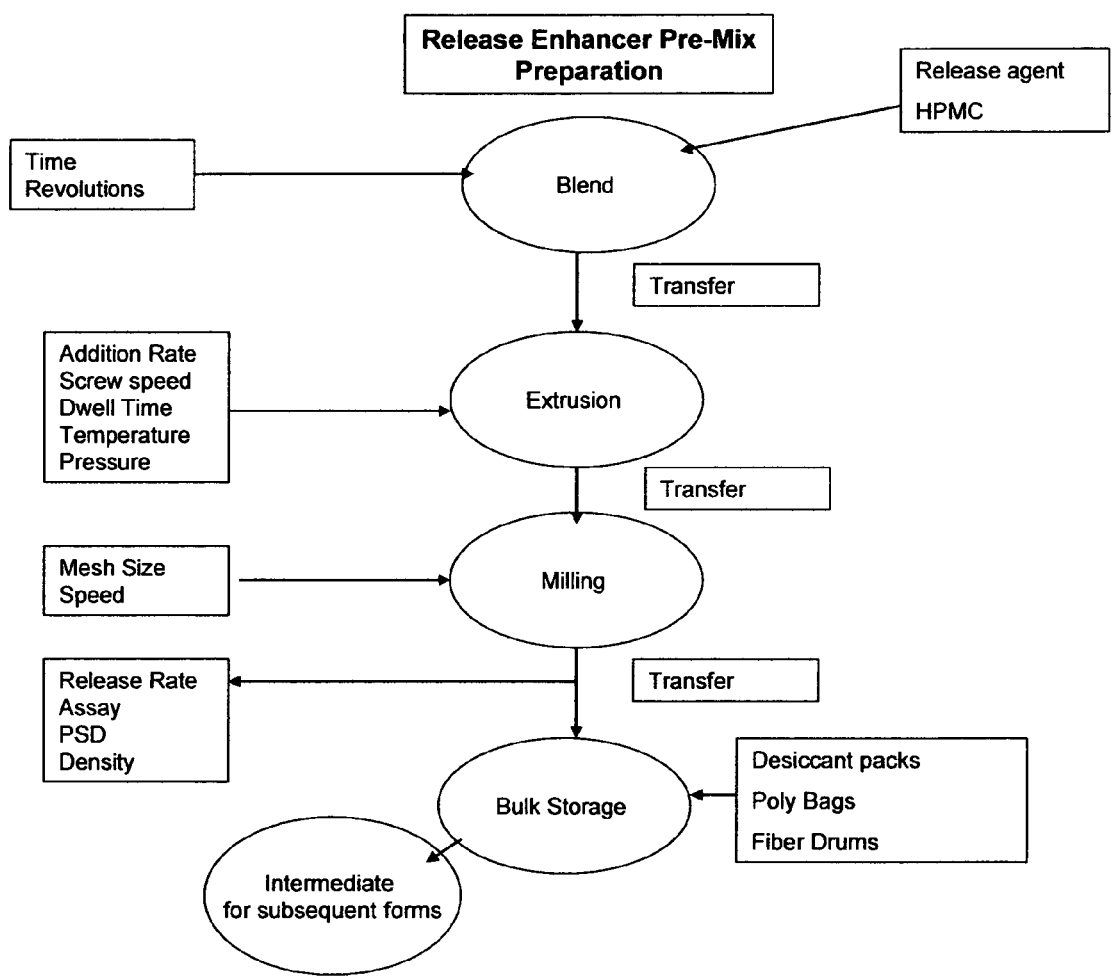
FIG. 5 is a flow chart that illustrates a process for creating a release enhancer which may be added to a drug resinate formulation.
Figure 7:
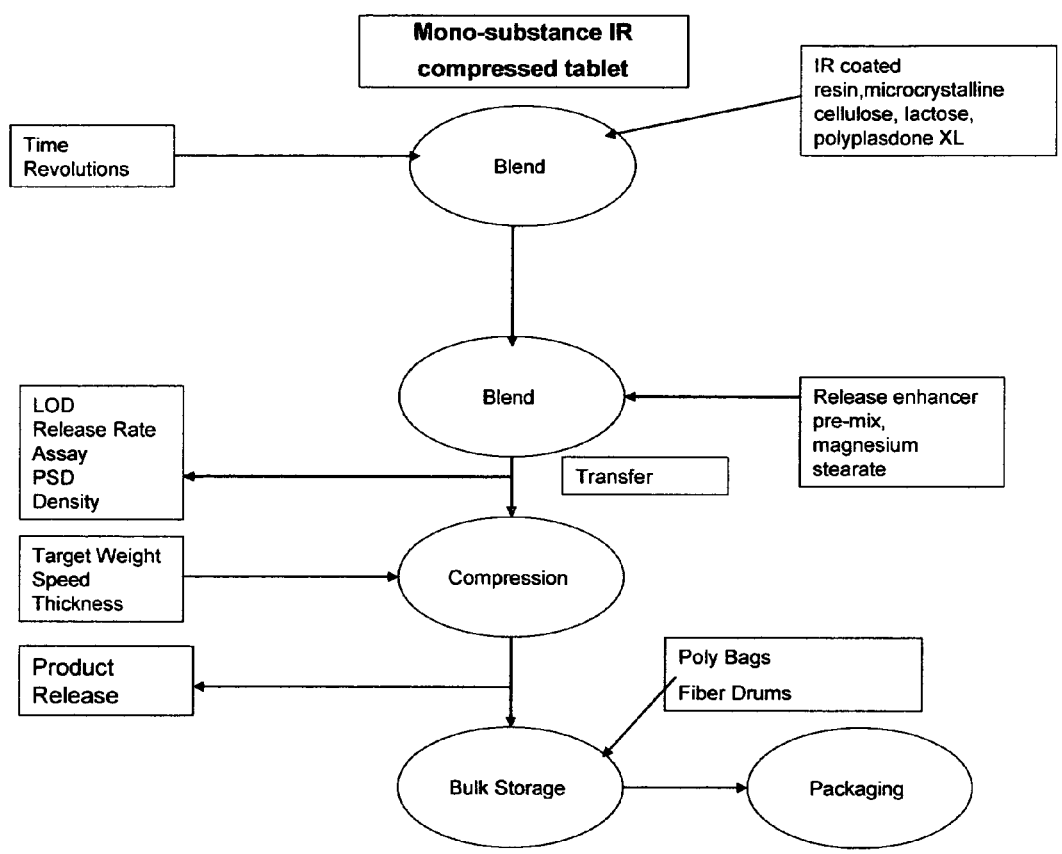
FIG. 7 is a flow chart that illustrates a process for creating an immediate release tablet dosage form containing a drug resinate and a release enhancing agent.

A mono-substance hydrocodone IR dosage form could be prepared as follows. The process begins with the coated hydrocodone resinate as specified in Example 1 and created with the processes described in FIG. 1 and FIG. 2. In the last process step, as shown in FIG. 7, the coated resinate, the release enhancer pre-mix (prepared by a process shown in FIG. 5) and the other excipients are blended and compressed into a tablet.

Example 4

Mono-Substance Pseudoephedrine IR Intermediate

| | |
|---|---|
| Pseudoephedrine HCl | 60 mg |
| Microcrystalline Cellulose | 250 mg |
| Polyvinylpyrrolidone | 20 mg |
| Magnesium Stearate | 4 mg |
| Colloidal Silicon Dioxide | 4 mg |
| HPMC 6 cps | 20 mg |
| Total Dosage Form Weight | 358 mg |

Figure 4:
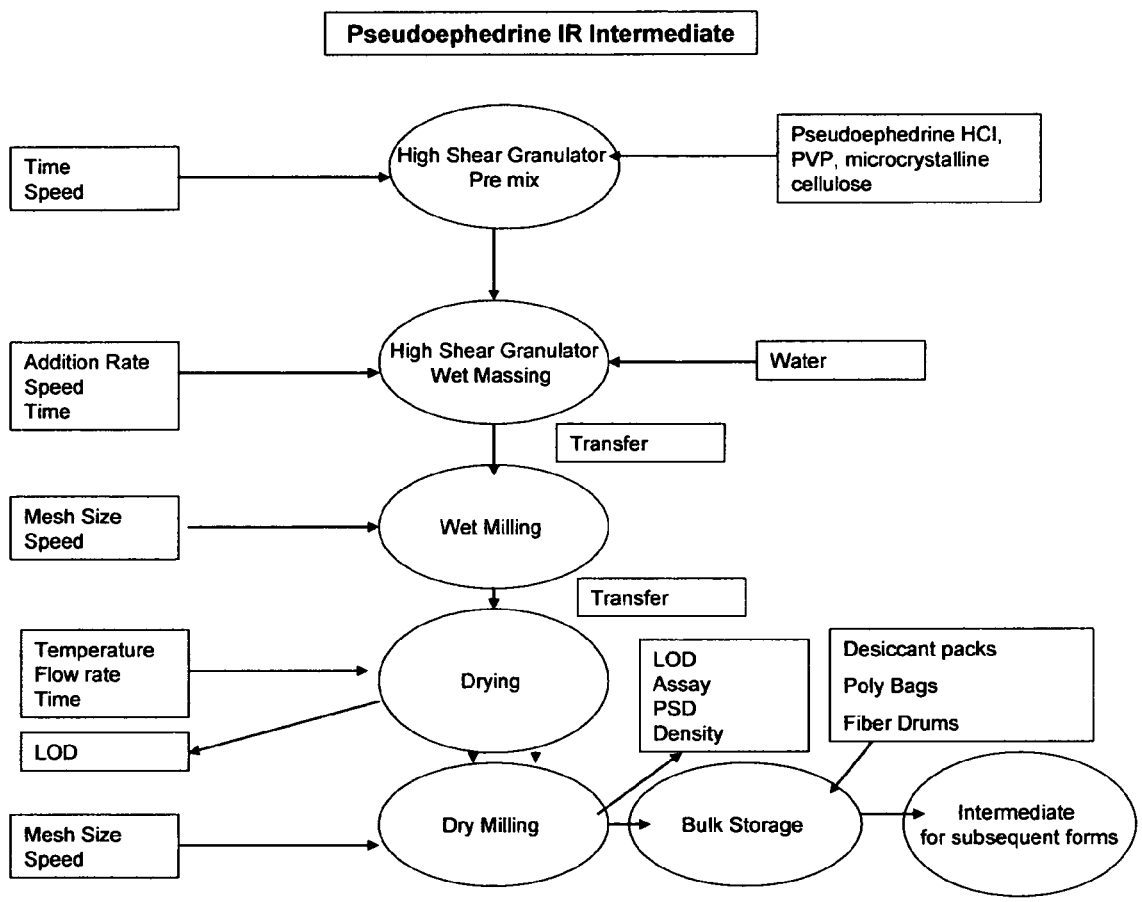
FIG. 4 is a flow chart that illustrates a process for creating a second drug component which may be added to a drug resinate formulation.

A mono-substance pseudoephedrine IR intermediate could be prepared as illustrated with the materials shown in Example 4 and using the process outlined in FIG. 4.

Example 5

Formulation for a Commercial Product

Fixed Combination Dosage Form Using the IR Hydrocodone Component with a Second Medicinal Agent, Hard Gelatin Capsule

| | |
|---|---|
| Hydrocodone Resinate Coated IR Intermediate* | 32 mg |
| Pseudoephedrine HCl Intermediate** | 358 mg |
| Microcrystalline Cellulose | 100 mg |
| Polyvinylpyrrolidone | 20 mg |
| Release enhancing agent | 15 mg |
| Magnesium Stearate | 4 mg |
| Colloidal Silicon Dioxide | 4 mg |
| Empty Capsule Shell #1 | 76 mg |
| Total Dosage Form Weight | 609 mg |

Figure 9:
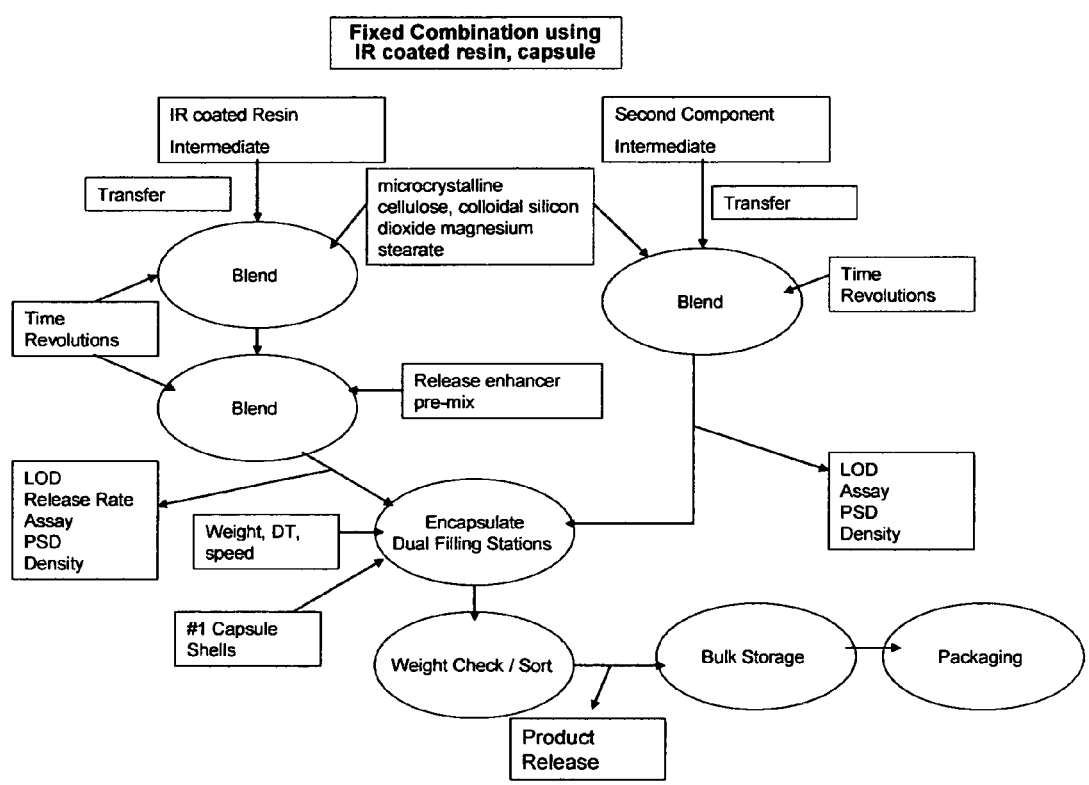
FIG. 9 is a flow chart that illustrates a process for creating an immediate release capsule dosage form containing an immediate release drug resinate, a second drug component and a release enhancing agent.

*Equivalent to Hydrocodone Bitartrate 10 mg
Equivalent to Pseudoephedrine HCl 60 mg A fixed combination hydrocodone IR dosage form could be prepared as follows. The process begins with the coated hydrocodone resinate as specified in Example 1 and created with the processes described in FIG. 1 and FIG. 2. The second drug component (pseudoephedrine HCl) is created as an Intermediate with the materials shown in Example 4 and the process outlined in FIG. 4. In the last process step, as shown in FIG. 9**, the coated resinate, the pseudoephedrine Intermediate and the release enhancing agent and the other excipients are blended and filled into hard gelatin capsules.

Example 6

Formulation for a Commercial Product

IR Hydrocodone Mono-Substance with a Second Medicinal Agent, Compressed Tablet

| | |
|---|---|
| Hydrocodone Resinate Coated IR Intermediate* | 32 mg |
| Pseudoephedrine HCl Intermediate** | 358 mg |
| Microcrystalline Cellulose | 250 mg |
| Polyvinylpyrrolidone | 20 mg |
| Release enhancing agent | 15 mg |
| Magnesium Stearate | 4 mg |
| Colloidal Silicon Dioxide | 4 mg |
| HPMC 6 cps | 20 mg |
| Total Dosage Form Weight | 703 mg |

Figure 8:
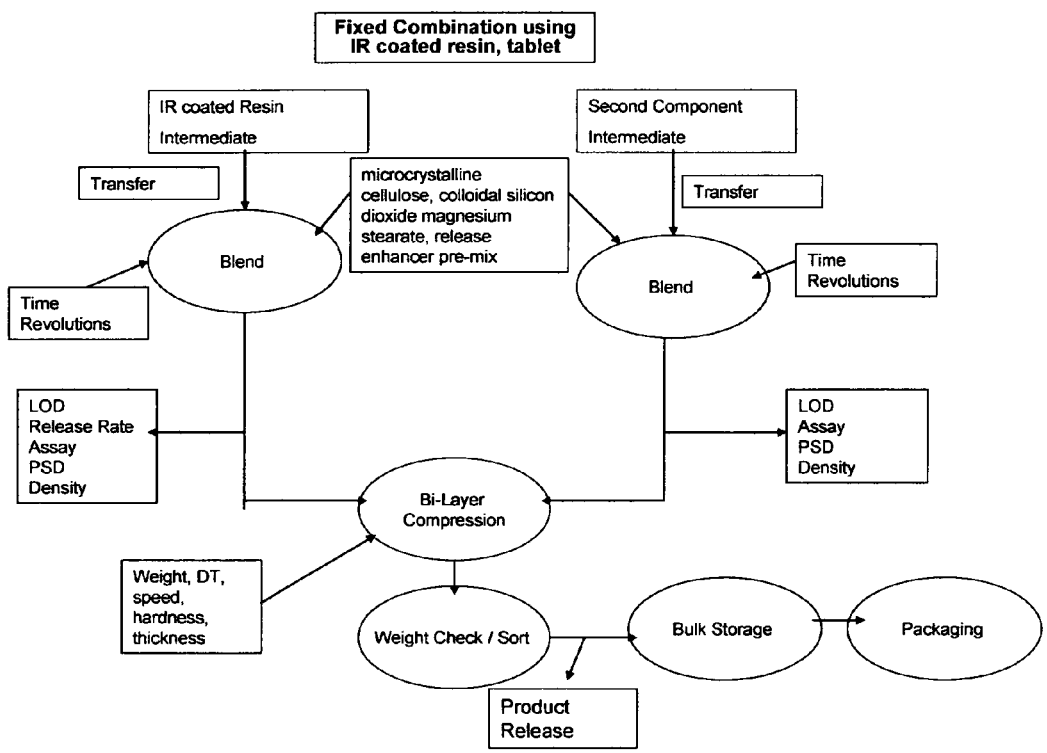
FIG. 8 is a flow chart that illustrates a process for creating an immediate release tablet dosage form containing a drug resinate, a second drug component and a release enhancing agent.

*Equivalent to Hydrocodone Bitartrate 10 mg
Equivalent to Pseudoephedrine HCl 60 mg A fixed combination hydrocodone IR dosage form could be prepared as follows. The process begins with the coated hydrocodone resinate as outlined in FIG. 2. The second drug component (pseudoephedrine HCl) is created as an Intermediate as specified in Example 4 and with the process shown FIG. 4. In the last process step, as shown in FIG. 8, the coated resinate, the Pseudoephedrine Intermediate component and the release enhancer pre-mix (prepared by a process shown in FIG. 5**) and the other excipients are blended and compressed into a tablet.

Example 7

IR Hydrocodone Mono-Substance Component Intermediate for Filling Hard Gelatin Capsules

| | |
|---|---|
| Hydrocodone Resinate Coated IR Intermediate* | 32 mg |
| Release enhancing agent | 15 mg |
| Magnesium Stearate | 2 mg |
| Colloidal Silicon Dioxide | 3 mg |
| IR component weight | 52 mg |

*Equivalent to Hydrocodone Bitartrate 10 mg

A mono-substance hydrocodone IR intermediate for capsules could be prepared as follows. The process begins with the coated hydrocodone resinate as specified in Example 1 and created with the processes described in FIG. 1 and FIG. 2. Next, the hydrocodone resinate intermediate, the release enhancing agent and the other excipients are blended to create an intermediate for filling capsules.

Example 8

ER Coated Hydrocodone Mono-Substance Component Intermediate for Filling Hard Gelatin Capsules

| | |
|---|---|
| IR Coated Resin Intermediate* | 32 mg |
| Methacrylic Acid Copolymer | 20 mg |
| Talc | 2 mg |
| Triethyl Citrate | 3 mg |
| Colloidal Silicon Dioxide | 3 mg |
| Magnesium Stearate | 2 mg |
| ER component weight* | 62 mg |

*Equivalent to Hydrocodone Bitartrate 10 mg

Figure 2:
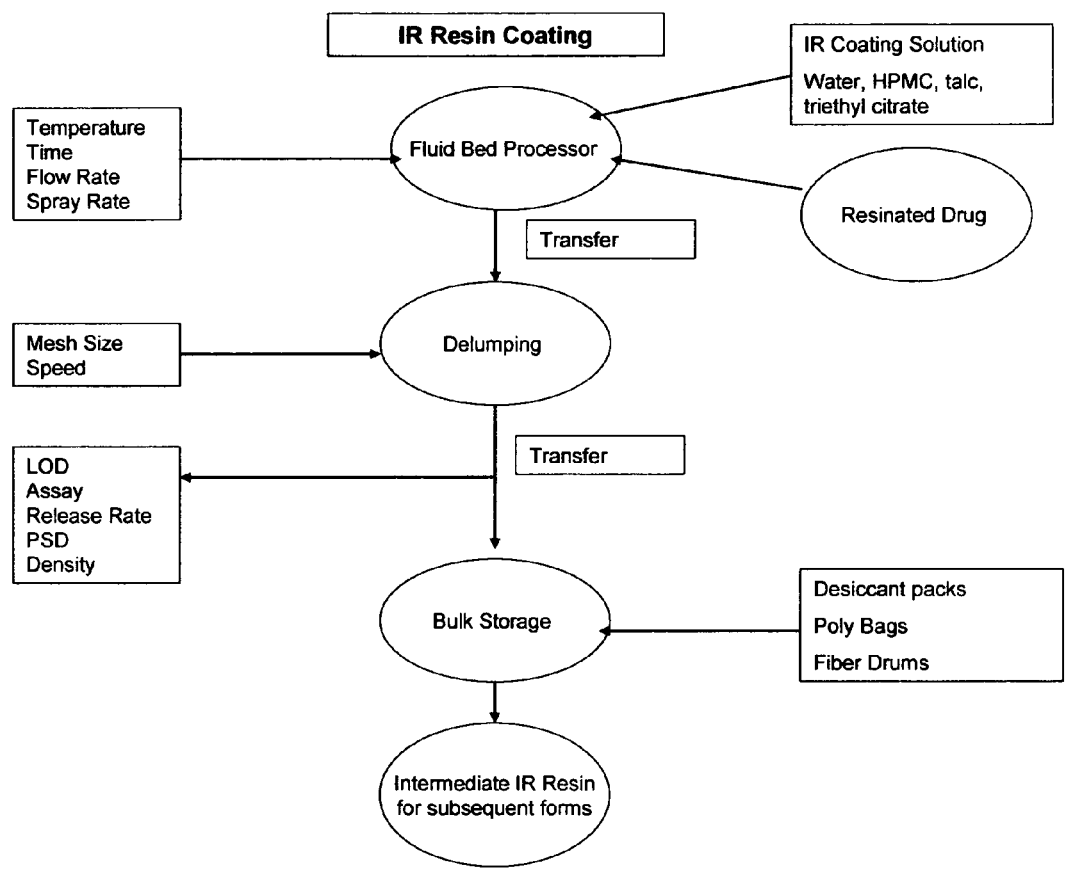
FIG. 2 is a flow chart that illustrates a process for adding a coating to a drug resinate to enhance material flow during additional manufacturing processes.
Figure 3:
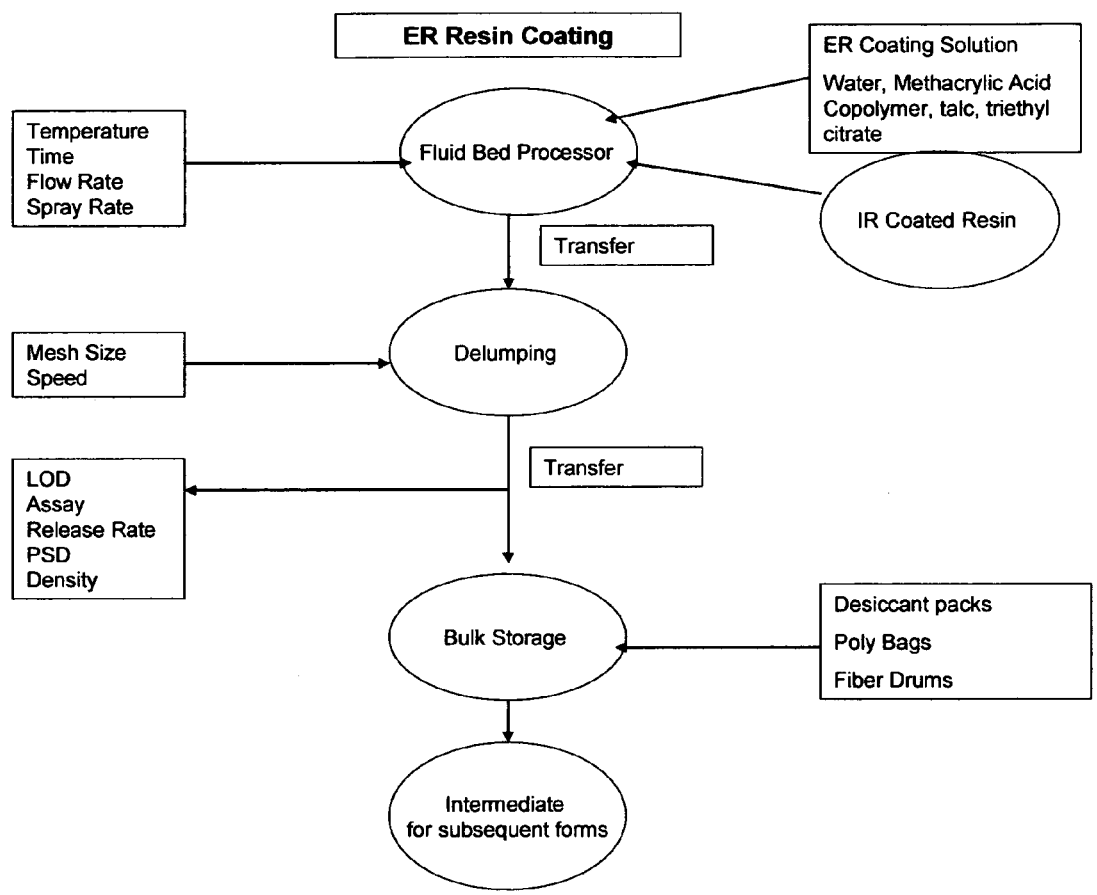
FIG. 3 is a flow chart that illustrates a process for adding an extended release coating to a drug resinate.

A mono-substance hydrocodone ER intermediate could be prepared as follows. The process begins with the coated hydrocodone resinate as specified in Example 1 and created with the process shown in FIG. 2. Next, the immediate release coated resinate intermediate is further coated as shown in FIG. 3 to create extended release (ER) intermediate particles.

Example 9

Formulation for a Commercial Product

IR/ER Hydrocodone Encapsulation to Fill a Hard Gelatin Capsule to Deliver 10 Mg Hydrocodone Total

| | |
|---|---|
| IR component weight* | 32 mg |
| ER component weight* | 62 mg |
| Empty Capsule Shell #1 | 76 mg |
| Total Dosage Form Weight | 170 mg |

*Equivalent to Hydrocodone Bitartrate 10 mg

Figure 10:
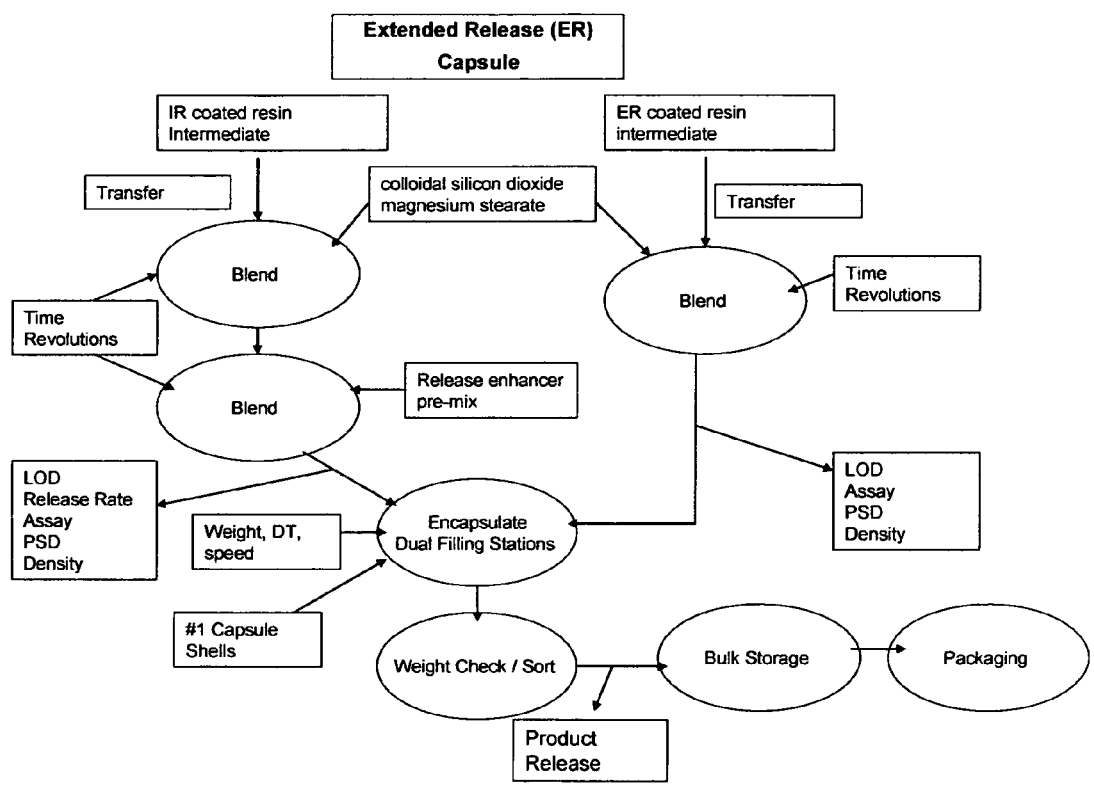
FIG. 10 is a flow chart that illustrates a process for creating a capsule dosage form containing an extended release drug resinate, an immediate release resinate component and a release enhancing agent.

A mono-substance hydrocodone ER dosage form could be prepared as follows. Starting with the hydrocodone IR intermediate specified in Example 1 and the ER intermediate specified in Example 8, the process for filling a capsule to create an extended release capsule (ER) is shown in FIG. 10. Notice that the process uses both the IR and ER coated hydrocodone intermediates from Examples 1 and 8, respectively.

Example 10

Mono-Substance Codeine IR Coated Intermediate

| | |
|---|---|
| Codeine Resinate Intermediate* | 60 mg |
| HPMC 6 cps | 3 mg |
| Talc | 2 mg |
| Triethyl Citrate | 2 mg |
| Total Dosage Form Weight | 67 mg |

*Equivalent to Codeine Phosphate 15 mg.

A mono-substance codeine IR intermediate could be prepared as follows. The process begins with the excipient and the active ingredient as described in Example 1. The process for creating the drug resinate is illustrated in FIG. 1. Next, the codeine resinate is coated to improve product flow as shown in FIG. 2.

Example 11

Formulation for a Commercial Product

IR Codeine Capsules

| | |
|---|---|
| Codeine Resinate Coated IR Intermediate* | 67 mg |
| Release enhancing agent | 15 mg |
| Magnesium Stearate | 2 mg |
| Colloidal Silicon Dioxide | 3 mg |
| Empty Capsule Shell #3 | 48 mg |
| Total Dosage Form Weight | 135 mg |

*Equivalent to Codeine Phosphate 15 mg.

A mono-substance codeine IR dosage form could be prepared as follows. The process begins with the coated codeine resinate as specified in Example 10. In the last process step, as shown in FIG. 6, the coated codeine resinate, the release enhancing agent and the other excipients are blended and filled into hard gelatin capsules.

Example 12

Formulation for a Commercial Product

IR Codeine Tablets

| | |
|---|---|
| Codeine Resinate Coated IR Intermediate* | 67 mg |
| Microcrystalline cellulose | 150 mg |
| Polyplasdone XL | 10 mg |
| Release enhancing agent | 15 mg |
| HPMC 6 cps | 20 mg |
| Anhydrous lactose | 100 mg |
| Magnesium stearate | 4 mg |
| Total Dosage Form Weight | 366 mg |

*Equivalent to Codeine Phosphate 15 mg

A mono-substance codeine IR dosage form could be prepared as follows. The process begins with the coated codeine resinate as specified in Example 10. In the last process step, as shown in FIG. 7, the coated codeine resinate, the release enhancing agent and the other excipients are blended and compressed into a tablet.

Example 13

Formulation for a Commercial Product

Fixed Combination Dosage form Using the IR Codeine Component with a Second Medicinal Agent, Hard Gelatin Capsule

| | |
|---|---|
| Codeine Resinate Coated IR Intermediate* | 67 mg |
| Pseudoephedrine HCl Intermediate** | 358 mg |
| Microcrystalline Cellulose | 100 mg |
| Polyvinylpyrrolidone | 20 mg |
| Release enhancing agent | 15 mg |
| Magnesium Stearate | 4 mg |
| Colloidal Silicon Dioxide | 4 mg |
| Empty Capsule Shell #1 | 76 mg |
| Total Dosage Form Weight | 644 mg |

*Equivalent to Codeine Phosphate 15 mg
Equivalent to Pseudoephedrine HCl 60 mg A fixed combination codeine IR dosage form could be prepared as follows. The process begins with the coated codeine resinate as specified in Example 10. The second drug component (pseudoephedrine HCl) is created as an intermediate as shown in Example 4. In the last process step, as shown in FIG. 9**, the coated codeine resinate, the pseudoephedrine component intermediate and the release enhancing agent and the other excipients are blended and filled into hard gelatin capsules.

Example 14

Formulation for a Commercial Product

Fixed Combination Dosage form Using the IR Codeine Component with a Second Medicinal Agent, Compressed Tablet

| | |
|---|---|
| Codeine Resinate Coated IR Intermediate* | 67 mg |
| Pseudoephedrine HCl Intermediate** | 358 mg |
| Microcrystalline Cellulose | 250 mg |
| Polyvinylpyrrolidone | 20 mg |
| Release enhancing agent | 15 mg |
| Magnesium Stearate | 4 mg |
| Colloidal Silicon Dioxide | 4 mg |
| HPMC 6 cps | 20 mg |
| Total Dosage Form Weight | 738 mg |

Equivalent to Codeine Phosphate 15 mg
**Equivalent to Pseudoephedrine HCl 60 mg

A fixed combination codeine IR dosage form could be prepared as follows. The process begins with the coated codeine resinate as specified in Example 10. The second drug component (pseudoephedrine HCl) is created as an Intermediate with the materials shown in Example 4 and the process outlined in FIG. 4. In the last process step, as shown in FIG. 8, the coated resinate, the second component Intermediate and the release enhancing agent and the other excipients are blended and compressed into a tablet.

Example 15

IR Codeine Mono-Substance Component Intermediate for Filling Hard Gelatin Capsules

| | |
|---|---|
| Codeine Resinate Coated IR Intermediate* | 67 mg |
| Release enhancing agent | 15 mg |
| Magnesium Stearate | 2 mg |
| Colloidal Silicon Dioxide | 3 mg |
| IR component weight | 87 mg |

*Equivalent to Codeine Phosphate 15 mg

A mono-substance codeine IR intermediate could be prepared as follows. The process begins with the coated codeine resinate as specified in Example 10 and created with the process outlined in FIG. 2. Next, the additional excipients are blended with the coated codeine resinate to produce the intermediate.

Example 16

ER Codeine Mono-Substance Component Intermediate for Filling Hard Gelatin Capsules

| | |
|---|---|
| IR Coated Codeine Resin component weight* | 67 mg |
| Methacrylic Acid Copolymer | 20 mg |
| Talc | 2 mg |
| Triethyl Citrate | 3 mg |
| Colloidal Silicon Dioxide | 3 mg |
| Magnesium Stearate | 2 mg |
| ER component weight | 97 mg |

*Equivalent to Codeine Phosphate 15 mg

A mono-substance codeine ER intermediate could be prepared as follows. The process begins with the coated codeine resinate using the formulation specified in Example 10 and the process outlined in FIG. 2. Next, the immediate release coated codeine resinate intermediate is further coated using the process shown in FIG. 3 to create an extended release (ER) intermediate.

Example 17

Formulation for a Commercial Product

IR/ER Codeine Encapsulation to Fill a Hard Gelatin Capsule to Deliver 30 Mg

| | |
|---|---|
| IR coated Codeine intermediate* | 67 mg |
| ER coated Codeine intermediate* | 97 mg |
| Empty Capsule Shell #1 | 76 mg |
| Total Dosage Form Weight | 240 mg |

*Equivalent to Codeine Phosphate 15 mg

A mono-substance codeine ER dosage form could be prepared as follows. The formulation for the IR codeine component is shown in Example 15 and the formulation for the ER codeine component is shown in Example 16. The process for filling a capsule with the IR and ER components used to create an extended release capsule (ER) is shown in FIG. 10. Notice that the process uses both the IR and ER coated intermediates from Examples 15 and 16, respectively.

Example 18

ER Coated Pseudoephedrine Component Intermediate for Filling Hard Gelatin Capsules

| | |
|---|---|
| IR coated Pseudoephedrine HCl* | 358 mg |
| Methacrylic Acid Copolymer | 20 mg |
| Talc | 2 mg |
| Triethyl Citrate | 3 mg |
| Colloidal Silicon Dioxide | 3 mg |
| Magnesium Stearate | 2 mg |
| ER component weight | 388 mg |

*Equivalent to Pseudoephedrine HCl 60 mg

Figure 11:
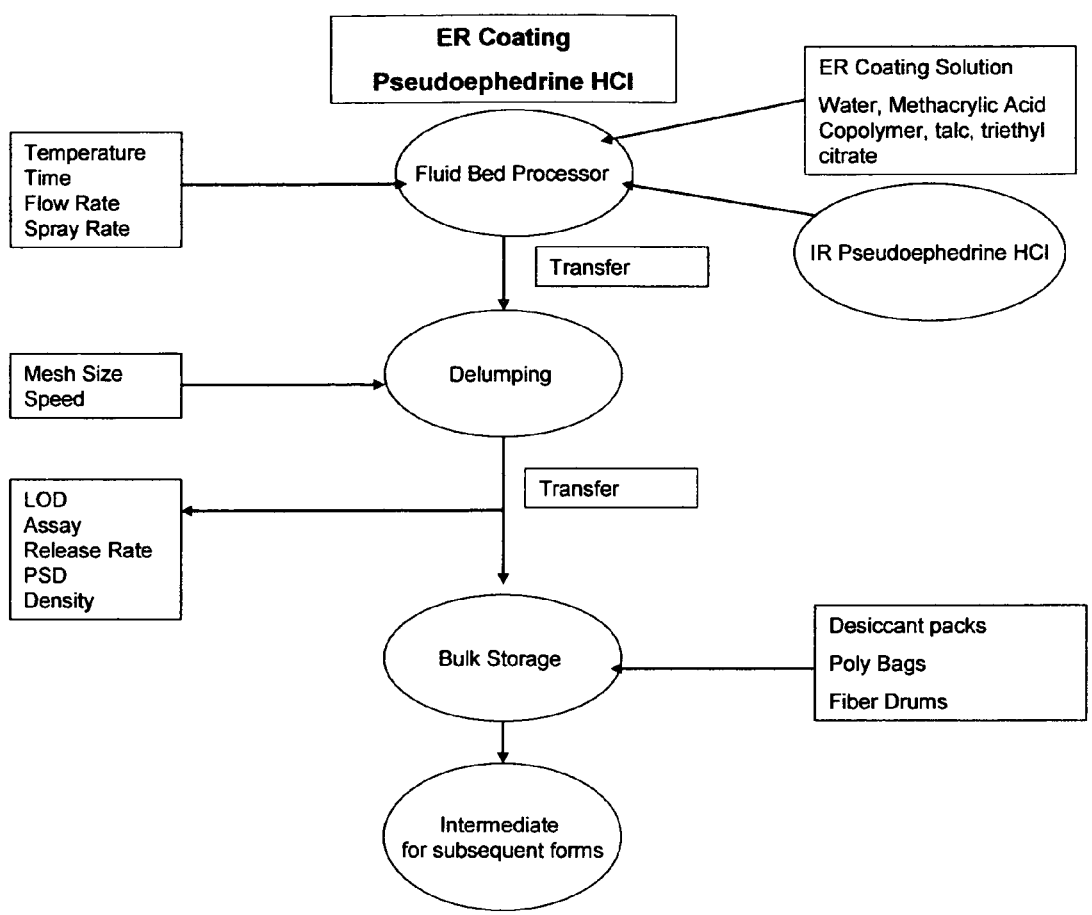
FIG. 11 is a flow chart that illustrates a process for creating an extended release pseudoephedrine component by coating immediate release pseudoephedrine particles.

A mono-substance pseudoephedrine ER intermediate could be prepared as follows. Starting with the active and inactive ingredients specified in this example 18, the process for creating the ER pseudoephedrine intermediate is illustrated in FIG. 11. The composition of the pseudoephedrine IR component is taken from Example 4.

Example 19

Formulation for a Commercial Product

IR/ER Hydrocodone, IR/ER Pseudoephedrine Encapsulation to Fill a Hard Gelatin Capsule to Deliver Hydrocodone 10 Mg, Pseudoephedrine 120 Mg

| | |
|---|---|
| IR Coated Hydrocodone component weight* | 32 mg |
| ER Coated Hydrocodone component weight* | 62 mg |
| IR Pseudoephedrine component weight** | 358 mg |
| ER pseudoephedrine component weight** | 388 mg |
| Empty Capsule Shell #00 | 130 mg |
| Total Dosage Form Weight | 970 mg |

*Equivalent to 10 mg hydrocodone
**Equivalent to 60 mg pseudoephedrine HCl

Figure 13:
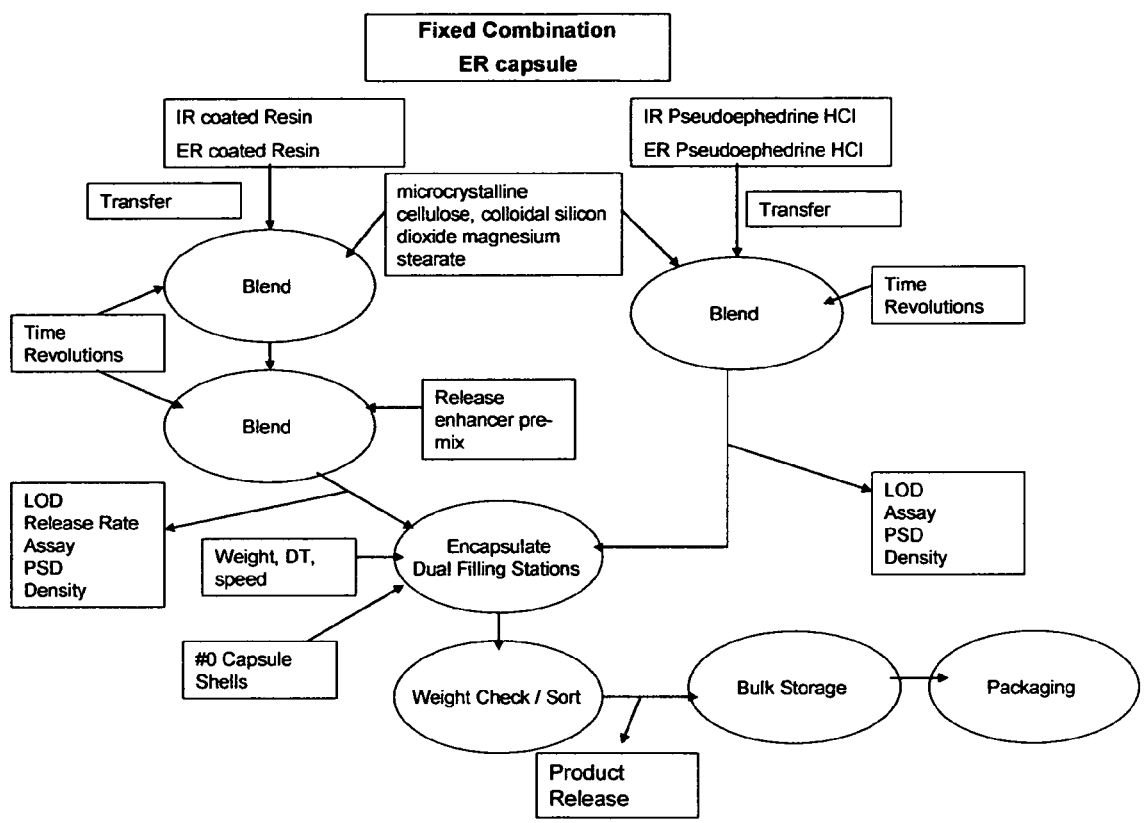
FIG. 13 is a flow chart that illustrates a process for creating a fixed combination ER capsule by combining IR and ER resinates along with IR and ER pseudoephedrine.

A fixed combination hydrocodone ER dosage form could be prepared as follows. The process for filling a capsule to create an extended release capsule (ER) fixed combination capsule is shown in FIG. 13. Notice that the process uses both the IR and ER coated hydrocodone intermediates from Examples 5 and 6, respectively and both the IR and ER pseudoephedrine intermediates from Examples 4 and 15, respectively.

Example 20

Formulation for a Commercial Product

IR/ER Hydrocodone, IR/ER Pseudoephedrine to Deliver Hydrocodone 10 Mg, Pseudoephedrine 120 Mg, Compressed Tablet

| | |
|---|---|
| IR Coated Hydrocodone Resinate Intermediate* | 32 mg |
| ER Coated Hydrocodone Resinate Intermediate* | 62 mg |
| IR Pseudoephedrine HCl Intermediate** | 358 mg |

-continued

| ER Pseudoephedrine HCl Intermediate** | 388 mg |
|---|---|
| Total Dosage Form Weight | 840 mg |

*Equivalent to 10 mg hydrocodone
**Equivalent to 60 mg pseudoephedrine HCl

Figure 12:
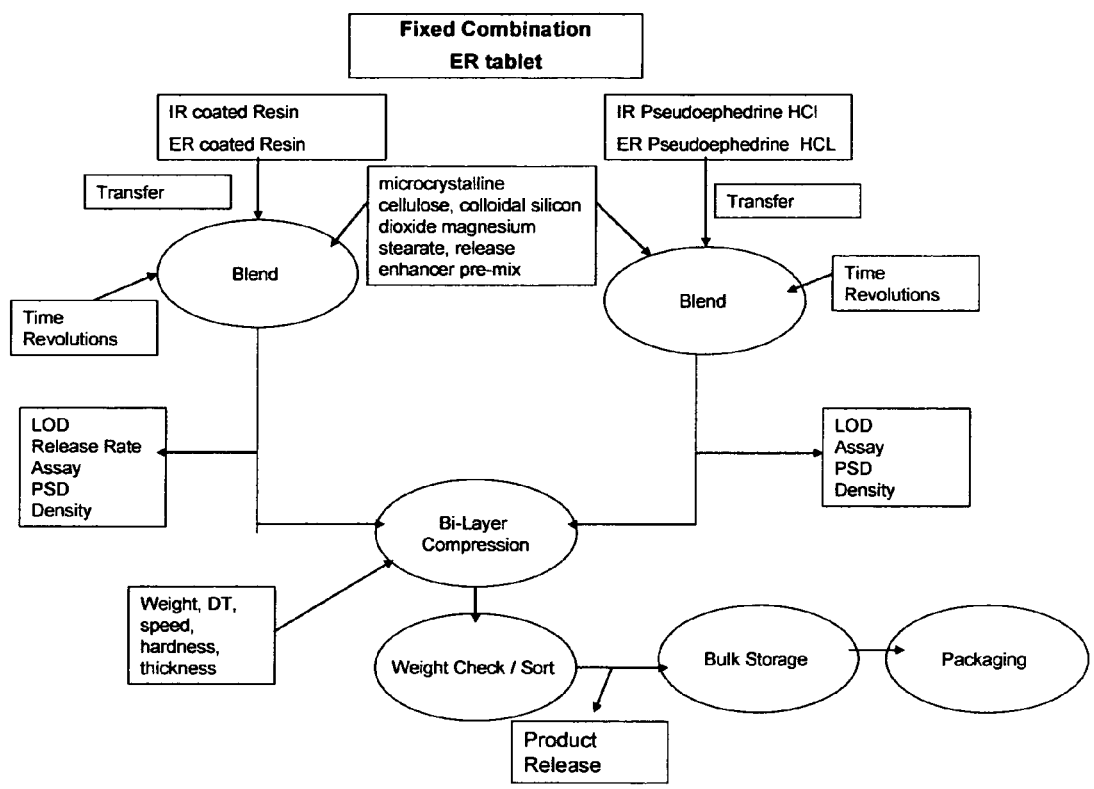
FIG. 12 is a flow chart that illustrates a process for creating a fixed combination ER tablet by combining IR and ER resinates along with IR and ER pseudoephedrine.

A fixed combination hydrocodone ER dosage form could be prepared as follows. The process for creating a compressed tablet to create an extended release (ER), fixed combination tablet is shown in FIG. 12. Notice that the process uses both the IR and ER coated hydrocodone intermediates for from Examples 5 and 6, respectively and both the IR and ER pseudoephedrine intermediates from Examples 4 and 15, respectively.

Example 21

Formulation for a Commercial Product

IR/ER Codeine, IR/ER Pseudoephedrine Encapsulation to Fill a Hard Gelatin Capsule to Deliver Codeine 30 mg, Pseudoephedrine 120 mg

| IR Coated Codeine Resinate Intermediate* | 87 mg |
|---|---|
| ER Coated Codeine Resinate Intermediate* | 97 mg |
| IR Pseudoephedrine Intermediate** | 358 mg |
| ER pseudoephedrine Intermediate** | 388 mg |
| Empty Capsule Shell #00 | 130 mg |
| Total Dosage Form Weight | 1,060 mg |

*Equivalent to 15 mg codeine
**Equivalent to 60 mg pseudoephedrine HCl

A fixed combination codeine ER dosage form could be prepared as follows. The process for filling a capsule to create an extended release capsule (ER) fixed combination capsule is shown in FIG. 13. Notice that the process uses both the IR and ER coated intermediates for codeine as shown in Examples 15 and 16, respectively and both the IR and ER pseudoephedrine intermediates from Examples 4 and 15, respectively.

Example 22

Formulation for a Commercial Product

IR/ER Codeine, ER/ER Pseudoephedrine to Deliver Codeine 30 mg, Pseudoephedrine 120 mg, Compressed Tablet

| IR Coated Codeine Coated Resinate* | 87 mg |
|---|---|
| ER Coated Codeine Coated Resinate* | 97 g |
| IR Pseudoephedrine HCl** | 358 mg |

-continued

| ER Pseudoephedrine HCl component** | 388 mg |
|---|---|
| Total Dosage Form Weight | 930 mg |

*Equivalent to 15 mg codeine
**Equivalent to 60 mg pseudoephedrine HCl

A fixed combination codeine ER dosage form could be prepared as follows. The process for creating a compressed tablet to create an extended release (ER), fixed combination tablet is shown in FIG. 12. Notice that the process uses both the IR and ER coated intermediates for codeine as shown in Examples 15 and 16, respectively and both the IR and ER pseudoephedrine intermediates from Examples 4 and 15, respectively.

Formulation Process

One process to manufacture the weak acid IER based products uses a modular approach in the preparation of the required intermediates. This allows maximal utilization of manufacturing capacity. It also assures minimal waste when processing controlled substances which are made to address selected therapeutic applications.

The intermediate materials are used in the manufacture of the final dosage form. The flexibility of the intermediates when combined with commonly used excipients and the release-enhancing agent allows for an array of oral solid dosage forms. Two of the most commonly used in the art are outlined in this process section.

The intermediate process and the dosage form preparation are shown here diagrammatically and fall into the following categories.

Intermediate Process Categories:
Resination of the Active Ingredient
Immediate Release (IR) Resin Coating
Extended release (ER) Resin Coating
Fixed Combination Second Component
Release Enhancer Pre-Mix
Dosage Form Process Categories:
Mono Substance IR Hard Gelatin Capsule
Mono Substance IR Compressed Tablet
Fixed Combination using the IR Resin Compressed Tablet
Fixed Combination using the IR Resin Hard Gelatin Capsule
Extended release Mono Substance Hard Gelatin Capsule

OTHER EMBODIMENTS

All publications, patent applications, and patents mentioned in this specification are herein incorporated by reference.

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology, or related fields are intended to be within the scope of the invention.

What is claimed is:

1. A solid oral dosage pharmaceutical composition comprising:
   (i) at least one pharmaceutically active agent bound to a weak acid ion exchange resin to form a weak acid ion-exchange resinate; and (ii) a release-enhancing agent consisting of FeCl$_3$;
wherein said pharmaceutical composition is capable of immediate release of said pharmaceutically active agent from said resinate at a pH of at least 1.5, immediate release being defined as at least 80% release of said pharmaceutically active agent within 45 minutes in a standard dissolution apparatus according to USP 31 NF 26 section 711.

2. The solid oral dosage pharmaceutical composition of claim 1, wherein said weak add ion exchange resin is terminated in a carbonic acid moiety.

3. The solid oral dosage pharmaceutical composition of claim 1 useful for oral administration.

4. The solid oral dosage pharmaceutical composition of claim 1, useful for patients having a condition selected from the group consisting of (original) *Helicobacter pylori* infection and atrophic gastritis.

5. The solid oral dosage pharmaceutical composition of claim 1 useful for administration to a patient within 24 hours of administration to said patient of a compound selected from the group consisting of a proton pump inhibitor, an H2 receptor antagonist, and an antacid.

6. The solid oral dosage pharmaceutical composition of claim 1 useful for administration to a patient having a condition selected from the group consisting of hypochlorhydria and achlorhydria in the stomach.

7. A solid oral dosage pharmaceutical composition comprising:
(i) at least one pharmaceutically active went bound to a weak acid ion exchange resin to form a weak acid ion-exchange resinate; and
(ii) a release-enhancing agent, wherein said release-enhancing agent is an organic base selected from the group consisting of thymine, guanine, and cytosine; and
wherein said pharmaceutical composition is capable of immediate release of said pharmaceutically active agent from said resinate at a pH of at least 1.5, immediate release being as at least 80% release of said pharmaceutically active agent within 45 minutes in a standard dissolution apparatus according to USP 31 NF 26 section 711.

8. The solid oral dosage pharmaceutical composition of claim 1, wherein said composition is formulated as a member of the group consisting of a capsule, a powder, a thin film, a caplet and a tablet.

9. The solid oral dosage pharmaceutical composition of claim 8, wherein said composition is formulated as a capsule.

10. The solid oral dosage pharmaceutical composition of claim 8, wherein said composition is formulated as a tablet.

11. The solid oral dosage pharmaceutical composition of claim 1, further comprising a second ion exchange resin; wherein said second ion exchange resin is bound to a pharmaceutically active agent and is coated with an extended release coating.

12. The solid oral dosage pharmaceutical composition of claim 11, wherein said second ion exchange resin is bound to the same pharmaceutically active agent as the first weak acid ion exchange resin.

13. A method of treating a patient with a stomach pH of at least about 1.5 comprising administration of a solid oral dosage composition, said solid oral dosage composition comprising:
(i) at least one pharmaceutically active agent bound to a weak acid ion exchange resin to form a weak acid ion-exchange resinate; and
(ii) a release-enhancing agent selected from the group consisting of an inorganic salt and an organic base;
wherein said administration results in immediate release of said pharmaceutically active agent from said weak acid ion exchange resinate, immediate release being defined as at least 80% release of said pharmaceutically active agent within 45 minutes in a standard dissolution apparatus according to USP 31 NF 26 section 711.

14. A method of treating a patient having a first condition and a second condition with a pharmaceutically active agent effective for treating said second condition, said method comprising the step of administering a solid oral dosage pharmaceutical composition, said solid oral dosage pharmaceutical composition comprising:
(i) at least one first pharmaceutically active agent bound to a weak acid ion exchange resin to form a weak acid ion-exchange resinate; and
(ii) a release-enhancing agent selected from the group consisting of an inorganic salt and an organic base;
wherein said administration results in immediate release of said pharmaceutically agent from said weak acid ion exchange resinate, immediate release being defined as at least 80% release of said pharmaceutically active agent within 45 minutes in a standard dissolution apparatus according to USP 31 NF 26 section 711; and
wherein said first condition is selected from the group consisting of *Helicobacter pylori* infection, atrophic gastritis, hypochlorhydria and achlorhydria in the stomach; and wherein said second condition is a condition other than said first condition.

15. A method of treating a patient wherein the patient has within the past 24 hours been administered a compound selected from the group consisting of a proton pump inhibitor, an H2 receptor antagonist, and an antacid, said method comprising the step of administering a solid oral dosage pharmaceutical composition, said solid oral dosage pharmaceutical composition comprising:
(i) at least one pharmaceutically active agent bound to a weak acid ion exchange resin to form a weak acid ion-exchange resinate; and
(ii) a release-enhancing agent selected from the group consisting of an inorganic salt and an organic base;
wherein said administration results in immediate release of said pharmaceutically active agent from said weak acid ion exchange resinate, immediate release being defined as at least 80% release of said pharmaceutically active within 45 minutes in a standard dissolution apparatus according to USP 31 NF 26 section 711.

16. A method of delivering a pharmaceutically active agent to a patient, said method comprising orally administering a compound selected from the group consisting of a proton pump inhibitor, an H2 receptor antagonist, and an antacid; and
a solid oral dosage pharmaceutical composition, said solid oral dosage pharmaceutical composition comprising:
(i) at least one pharmaceutically active agent bound to a weak acid ion exchange resin to form a weak acid ion-exchange resinate; and
(ii) a release-enhancing agent selected from the group consisting of an inorganic salt and an organic base; and
wherein said administration results in immediate release of said pharmaceutically active agent from said weak acid ion exchange resinate, immediate release being defined as at least 80% release of said pharmaceutically active agent within 45 minutes in a standard dissolution apparatus according to USP 31 NF 26 section 711;
and wherein said solid oral dosage composition is administered within 24 hours of said proton pump inhibitor, H2 receptor antagonist, or antacid.

* * * * *